United States Patent [19]

Eberlein et al.

[11] Patent Number: 4,904,673
[45] Date of Patent: Feb. 27, 1990

[54] AGENT FOR TREATING BRADYCARDIA AND BRADYARRHYTHMIA

[75] Inventors: Wolfgang Eberlein; Wolfhard Engel; Gerhard Mihm; Norbert Mayer, all of Biberach; Adriaan de Jonge, Driebergen, all of Fed. Rep. of Germany

[73] Assignee: Dr. Karl Thomae, GmbH, Biberach an der Riss, Fed. Rep. of Germany

[21] Appl. No.: 298,078

[22] Filed: Jan. 17, 1989

[30] Foreign Application Priority Data

Jan. 14, 1988 [DE] Fed. Rep. of Germany ....... 3800868

[51] Int. Cl.$^4$ ............................................. A61K 31/445
[52] U.S. Cl. ..................................................... 514/330
[58] Field of Search ......................................... 514/330

[56] References Cited

U.S. PATENT DOCUMENTS 4,547,514 10/1985 Mathur ................................. 514/316
4,560,692 12/1985 Field ..................................... 514/313

FOREIGN PATENT DOCUMENTS 705408  1/1968  Canada .
160436 11/1985  European Pat. Off. .
177078  4/1986  European Pat. Off. .
931789  1/1968  United Kingdom .
932487  1/1968  United Kingdom .
949729  1/1968  United Kingdom .

OTHER PUBLICATIONS

De Bree, CA. 110:224807w (1988).
Van Der Stel, CA. 110:204964s (1988).
Buffington, CA. 110:147636k (1989).
Bigler, CA. 106:107814c (1986).
Thomas, CA. 106:12842w (1986).

Primary Examiner—Shep K. Rose
Attorney, Agent, or Firm—D. E. Frankhouser; Mary-Ellen M. Timbers; Alan R. Stempel

[57] ABSTRACT (±)-1-[4-[Ethyl[2-(4-methoxyphenyl)-1-methylethyl]-amino]-1-oxobutyl]-N,N-dimethyl-4-piperidine carboxamide and (+)-1-[4-[ethyl[2-(4-methoxyphenyl)-1-methylethyl]-amino]-1-oxobutyl]N,N-dimethyl-4-piperidinecarboxamide, as well as the physiologically acceptable acid addition salts of these compounds are suitable for the treatment of bradycardia and bradyarrhythmia.

2 Claims, No Drawings

AGENT FOR TREATING BRADYCARDIA AND BRADYARRHYTHMIA

The invention relates to an agent for treating bradycardia and bradyarrhythmia which contains the compounds (+)-1-[4-[ethyl[2-(4-methoxyphenyl)-1-methylethyl]amino]-1-oxobutyl]-N,N-dimethyl-4-piperidinecarboxamide (I) and (+)-1-[4-[ethyl[2-(4-methoxyphenyl)-1-methylethyl]amino]-1-oxobutyl]-N,N-dimethyl-4-piperidinecarboxamide (II) and the physiologically acceptable salts thereof with inorganic or organic acids.

European Patent Application No. 85 201 394.5 (Publication No. 0 177 078) describes compounds which, being muscarinic receptor antagonists, have specific spasmolytic properties and may therefore advantageously be used for treating spasm in the gastrointestinal tract.

It has been found, surprisingly, that the compounds contained in the above-mentioned patent application, namely I. (±)-1-[4-[ethyl[2-(4-methoxyphenyl)-1-methylethyl]amino]-1-oxobutyl]-N,N-dimethyl-4-piperidinecarboxamide and II. (+)-1-[4-[ethyl[2-(4-methoxyphenyl)-1-methylethyl]amino]-1-oxobutyl]-N,N-dimethyl-4-piperidinecarboxamide and the physiologically acceptable salts thereof with inorganic or organic acids also have entirely different pharmacological properties which enable them to be used as vagal pacemakers for the treatment of bradycardia and bradyarrhythmia.

The above-mentioned compounds I and II have surprisingly been found to show marked selectivity for the muscarinic receptors in the heart. The substantial gap between the desired effects on heart rate and the undesirable anticholinergic effects enables the compounds I and II to be used as vagal pacemakers for treating various types of bradycardia and bradyarrhythmia without resulting in unacceptable side effects.

A favorable relation between tachycardiac effects on the one hand and on the other hand the undesirable effects on pupil size and the secretion of tears, saliva and gastric acid which occur in therapeutic agents with an anticholinergic component is of particular importance in the therapeutic use of the substances.

The following tests show that the compounds according to the invention show surprisingly good relations of this kind.

A. Studies of binding to muscarinic receptors:

In vitro measurement of the $IC_{50}$ value

The organs were donated by male Sprague-Dawley rats weighing 180-220 g. After the heart and submandibular gland and cerebral cortex had been removed, all other steps were carried out in ice cold Hepes HCl buffer (pH 7.4; 100 millimolar NaCl, 10 millimolar $MgCl_2$). The whole heart was cut up with scissors. All the organs were then homogenised in a Potter apparatus.

For the binding test the homogenised organs were diluted as follows:
Whole heart 1:400
Cerebral cortex 1:3000
Submandibular gland 1:400
The homogenised organs were incubated at a certain concentration of the radioligand and at a series of concentrations of the non-radioactive test substances in an Eppendorf centrifuge tube at 30° C. Incubation lasted 45 minutes. The radioligand used was 0.3 nanomolar $^3$H-N-methylscopolamine ($^3$H-NMS). Incubation was ended by the addition of ice cold buffer followed by vaccum filtration. The filters were rinsed with cold buffer and their radioactivity was determined. It represents the sum of specific and non-specific binding of $^3$H-NMS.

The proportion of non-specific binding was defined as the radioactivity which was bound in the presence of 1 micromolar quinuclidinyl-benzylate. Each measurement was taken four times. The $IC^{50}$ values of the non-labelled test substances were determined graphically. They represent that concentration of test substance at which the specific binding of $^3$H-NMS to the muscarinic receptors in the various organs was inhibited by 50%. The results can be seen from Table 1.

B. Investigation of functional selectivity of the antimuscarinic effect

Substances with antimuscarinic properties inhibit the effects of agonists supplied exogenically or of acetylcholine, which is released from cholinergic nerve endings. The following is a description of an "in vivo" method which is suitable for the detection of cardioselective antimuscarinic agents.

The objective of the method used was to confirm the selectivity of the antimuscarinic effect.

Inhibition of the effect of acetylcholine on the bladder, bronchi and heart rate in guinea pigs 5 minutes after the administration of the test substance, 10 microgram/kg of acetylcholine were simultaneously injected intravenously and intra-arterially into anaesthetised guinea pigs. The heart rate was recorded directly by extracorporeal derivation of the ECG, as were the expiration resistance according to Konzett-Rossler and the contraction of the exposed bladder. In order to determine the inhibition of the acetylcholine activity on the organs under investigation, dosage/activity curves were recorded and from them $-\log ED_{50}$ values were determined. For the results see Table II.

The following compounds for example were investigated as described above:

A=(±)-1-[4-[ethyl[2-(4-methoxyphenyl)-1-methylethyl]amino]-1-oxobutyl]-N,N-dimethyl-4-piperidine carboxamide and B=atropine.

TABLE I

| Receptor Binding Tests in vitro: Results: | | | |
|---|---|---|---|
| | Receptor Binding Tests $IC50$ [$nMl^{-1}$] | | |
| Substance | Cortex | Heart | Submandibular gland |
| A | 50 | 10 | 300 |
| B | 2 | 4 | 4 |

The information in Table I above shows that the new compounds distinguish between muscarinic receptors in different tissues. This is clear from the substantially lower $IC_{50}$ values when the test substances are investigated on preparations from the heart compared with those from the cerebral cortex. However, the binding data in particular show that the heart rate is increased by the above-mentioned compound at dosages at which no restriction of salivation can be expected.

TABLE II

| | Results: | | |
|---|---|---|---|
| | $-\log ED_{50}[\text{molkg}^{-1}]$ | | |
| Substance | Heart | Bronchi | Bladder |
| A | 7.19 | 6.83 | 6.29 |

The pharmacological data in Table II above indicate a surprisingly higher power of distinction between the heart and the smooth muscle of the bladder.

For pharmaceutical use, the compounds I and II may be incorporated, in known manner, in the conventional pharmaceutical preparations, e.g. solutions, suppositories, tablets, coated tablets, capsules or infusions. The daily dosage is generally between 0.02 and 5 mg/kg, preferably 0.02 and 2.5 mg/kg, more particularly 0.05 and 1.0 mg/kg of body weight, optionally administered in the form of several, preferably 1 to 3, individual doses, to achieve the desired results.

The preparation of compounds I and II is described in European Patent Application No. 85 201 394.5 (Publication No. 0 177 078).

The following Examples illustrate the preparation of some pharmaceutical administration forms:

EXAMPLE I

Tablets containing 20.0 mg of
(+)-1-[4-[ethyl[2-(4-methoxyphenyl)-1-methylethyl]amino]-1-oxobutyl]-N,N-dimethyl-4-piperidinecarboxamide

| Composition: 1 tablet contains: | |
|---|---|
| Active substance | 20.0 mg |
| Lactose | 152.0 mg |
| Potato starch | 65.0 mg |
| Magnesium stearate | 2.0 mg |
| | 239.0 mg |

Method of preparation

A 10% mucilage is prepared from potato starch by heating. The active substance, lactose and remaining potato starch are mixed together and granulated with the above mucilage through a 1.5 mm mesh screen. The granules are dried at 45° C., rubbed through the same screen again, mixed with magnesium stearate and compressed to form tablets.
Weight of tablet: 239 mg
Punch: 9 mm

EXAMPLE II

Coated tablets containing 20.0 mg of
(±)-1-[4-[ethyl[2-(4-methoxyphenyl)-1-methylethyl]amino]-1-oxobutyl]-N,N-dimethyl-4-piperidinecarboxamide The tablets prepared according to Example I are coated, by a known method, with a coating consisting essentially of sugar and talc. The finished coated tablets are polished with beeswax. Weight of coated tablet: 300 mg

EXAMPLE III

Ampoules containing 4.0 mg of
(+)-1-[4-[ethyl[2-(4-methoxyphenyl)-1-methylethyl]amino]-1-oxobutyl]-N,N-dimethyl-4-piperidinecarboxamide

| Composition: 1 ampoule contains: | |
|---|---|
| Active substance | 4.0 mg |
| Sodium chloride | 8.0 mg |
| Distilled water ad | 1 ml |

Method of preparation

The active substance and sodium chloride are dissolved in distilled water and then made up to the volume specified. The solution is sterile filtered and transferred into 1 ml ampoules. Sterilization: 20 minutes at 120° C.

EXAMPLE IV

Suppositories containing 20 mg of
(±)-1-[4-[ethyl[2-(4-methoxyphenyl)-1-methylethyl]amino]-1-oxobutyl]-N,N-dimethyl-4-piperidinecarboxamide

| Composition: 1 suppository contains: | |
|---|---|
| Active substance | 20.0 mg |
| Suppository mass (e.g. Witepsol W 45(R)) | 1 690.0 mg |
| | 1 710.0 mg |

Method of preparation

The finely powdered active substance is suspended in the molten suppository mass which has been cooled to 40° C. The mass is poured at 37° C. into slightly chilled suppository moulds. Weight of suppository 1.71 g

EXAMPLE V

Drops containing
(±)-1-[4-[ethyl[2-(4-methoxyphenyl)-1-methylethyl]amino]-1-oxobutyl]-N,N-dimethyl-4-piperidinecarboxamide

| Composition: 100 ml of drops solution contain: | |
|---|---|
| Methyl p-hydroxybenzoate | 0.035 g |
| Propyl p-hydroxybenzoate | 0.015 g |
| Aniseed oil | 0.05 g |
| Menthol | 0.06 g |
| Pure ethanol | 10.0 g |
| Active substance | 0.8 g |
| Sodium cyclamate | 1.0 g |
| Glycerol | 15.0 g |
| Distilled water ad | 100.0 ml |

Method of preparation

The active substance and sodium cyclamate are dissolved in about 70 ml of water and glycerol is added. The p-hydroxybenzoates, aniseed oil and methanol are dissolved in ethanol and this solution is added with stirring to the aqueous solution. Finally, the solution is made up to 100 ml with water and filtered to remove any suspended particles.

What is claimed is:

1. A method for treatment of bradycardia in a warm-blooded animal comprising administering to said animal a therapeutically effective amount of a compound selected from the group consisting of (±)-1-[4-[ethyl[2-(4-methoxyphenyl)-1-methylethyl]amino]-1-oxobutyl]-N,N-dimethyl-4-piperidinecarboxamide, and (+)-1-[4-[ethyl[2-(4-methoxyphenyl)-1-methylethyl]amino]-1-oxobutyl]-N,N-dimethyl-4-piperidinecarboxamide or physiologically acceptable salts of these compounds with inorganic or organic acids.

2. A method for treatment of bradyarrhythmia in a warm-blooded animal comprising administering to said animal to therapeutically effective amount of a compound selected from the group consisting of (±)-1-[4-[ethyl[2-(4-methoxyphenyl)-1-methylethyl]amino]-1-oxobutyl]-N,N-dimethyl-4-piperidinecarboxamide, and (+)-1-[4-[ethyl[2-(4-methoxyphenyl)-1-methylethyl]amino]-1-oxobutyl]-N,N-dimethyl-4-piperidinecarboxamide or physiologically acceptable salts of these compounds with inorganic or organic acids.

* * * * *